United States Patent [19]

Kawaguchi

[11] Patent Number: 5,030,089
[45] Date of Patent: Jul. 9, 1991

[54] ORTHODONTIC APPLIANCE WITH HOOK

[75] Inventor: Kozo Kawaguchi, Ohkumamchi, Japan

[73] Assignee: GAC International, Inc., Central Islip, N.Y.

[21] Appl. No.: 514,186

[22] Filed: Apr. 25, 1990

Related U.S. Application Data

[63] Continuation-in-part of Ser. No. 350,939, May 12, 1989.

[30] Foreign Application Priority Data

May 12, 1989 [JP] Japan ............................... 1-54000

[51] Int. Cl.$^5$ .................................................. A61C 3/00
[52] U.S. Cl. .......................................... 433/8; 433/18; 433/19
[58] Field of Search ................ 433/8, 9, 11, 22, 18, 433/19, 10

[56] References Cited

U.S. PATENT DOCUMENTS

| D. 290,040 | 5/1987 | Kelly | D24/16 |
| D. 304,077 | 10/1989 | Pospisil | D24/16 |
| 3,530,583 | 9/1970 | Klein et al. | 433/18 |
| 4,487,581 | 12/1984 | Adler | 433/16 |
| 4,799,882 | 1/1989 | Kesling | 433/8 |

OTHER PUBLICATIONS

The Masel Orthodontics, Inc. advertisement.
The Lancer Orthodontics, Inc. advertisement.
The Dentaurum, Inc. advertisement.
The Ortho Organizers, Inc. advertisement.
The RMO, Inc. advertisement.
The Unitek Corporation advertisement.
The "Intrigue" advertisement.

*Primary Examiner*—Cary E. Stone
*Attorney, Agent, or Firm*—Kenyon & Kenyon

[57] ABSTRACT

An orthodontic appliance has a base portion having formed on one side thereof a tooth-abutting surface and a bracket portion defining an archwire slot therein. Two tie-wings project outwardly from the bracket portion and extend along one side of the archwire slot. Two hooked tie-wings extend along the other side of the archwire slot and project outwardly therefrom. Each hooked tie-wing defines on an interior side thereof a hook-shaped surface. The hook-shaped surfaces are provided for mounting auxiliary force transmitting members thereto.

33 Claims, 5 Drawing Sheets

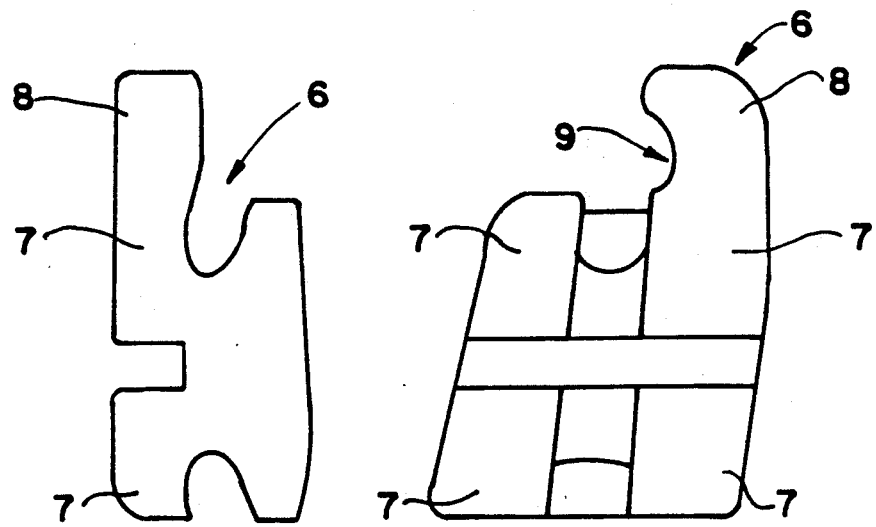
(PRIOR ART)
FIGURE 4
(PRIOR ART)
FIGURE 3
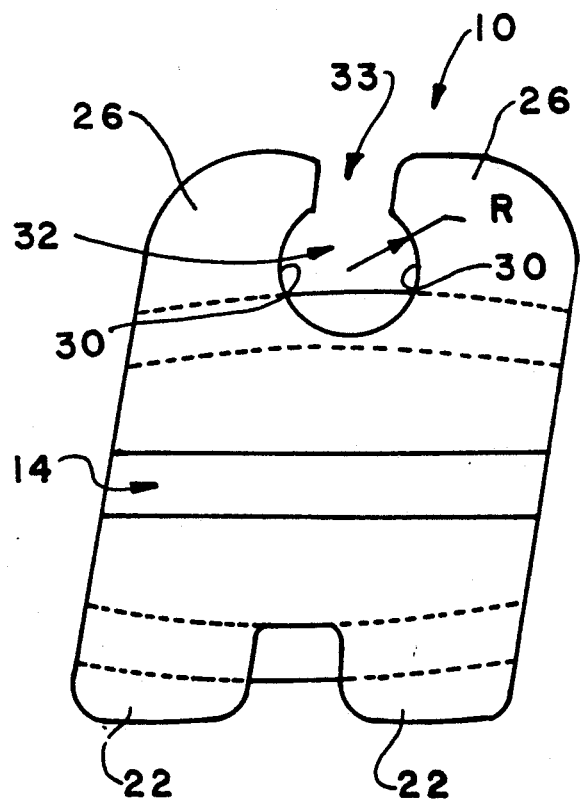
FIGURE 10

FIGURE 6 (A-A)

ORTHODONTIC APPLIANCE WITH HOOK

This application is a continuation-in-part of U.S. application Ser. No. 07/350,939, filed May 12, 1989, co-pending herewith.

1. Field of the Invention

The present invention relates to orthodontic appliances and, more particularly, to orthodontic appliances having hooks or posts for connecting the appliances to other orthodontic appliances.

2. Background Information

Hooks or posts have generally been employed on orthodontic appliances for transmitting forces to the appliance by attaching, for example, a ligature, elastic, or coil spring thereto. The hook or post is generally mounted on one of the tie-wings so that it projects outwardly therefrom, generally perpendicular to the axial direction of the archwire slot. The forces transmitted to the hook or post are in turn transmitted by the appliance to the tooth to move the tooth as desired. Such hooks or posts have predominantly been employed on metal orthodontic appliances and only recently have been used with ceramic appliances.

The location of the hook on the appliance is determined depending upon the direction that the tooth is to be moved. The hooks or posts are usually located on the gingival tie-wings on the side of the appliance facing the direction that the tooth should be moved. For example, if the tooth is to be moved posteriorly, the hook is mounted on the distogingival tie-wings. If, on the other hand, the tooth is to be moved mesially, the hook is mounted on the mesiogingival tie-wings. The hook or post may then be employed for attaching an elastic, ligating the archwire, or connecting one end of a coil spring thereto. The hook or post is therefore used to achieve any of a number of objectives including, for example, retracting a canine into an extraction site, moving a bicuspid, or rotating a tooth.

When used on metal appliances, metal hooks or posts may be made relatively small. Because the metal used is relatively strong, the hooks or posts ordinarily withstand the forces exerted upon them. However, larger metal hooks may contact the tissue in a patient's mouth, causing the patient discomfort. If a small metal hook or post is properly positioned on an appliance, it generally will avoid impinging on the tissue in the patient's mouth. The smallest metal hooks generally do not add significant bulk to the appliance and, therefore, usually do not cause the patient additional discomfort.

One advantage of employing a hook or post on an orthodontic appliance is that it can transmit a force substantially parallel to the archwire slot, yet closer to the gingival side of the tooth. The gingival side of the tooth is closer to the center of resistance of the tooth than is the area adjacent to the archwire slot. Therefore, by employing the hook, the appliance force can be transmitted closer to the resistance area of the tooth and, thus, will usually more efficiently move the tooth. Another advantage of a hook or post is that it may obviate the need for an additional appliance to mount thereto a force transmitting member, such as a coil spring.

Metal hooks or posts have been made in a variety of sizes and shapes. For example, the free ends of such posts are frequently expanded into a ball-shape or other shape having an increased cross-sectional area to facilitate the attachment of ligature, elastics, coil springs, or other force transmitting members thereto. Metal hooks or posts are usually mounted to the tie-wings by either welding, soldering, or brazing. If the bracket is formed by casting, the hook or post can be formed as an integral part thereof.

An orthodontist is often required to reverse the direction of the force applied by an appliance during treatment. One problem with appliances having metal hooks or posts, however, is that the appliance either has to be replaced with an appliance having a hook or post located on the opposite side thereof, or the orthodontist is required to leave the appliance on the tooth without using the hook. If the appliance is not replaced, the orthodontist is forced to compromise the optimal performance of the appliance.

For example, if an appliance is initially mounted to move a tooth posteriorly, the post or hook is normally located on the distogingival tie-wings. However, if during treatment it is determined that the tooth should then be moved anteriorly, the most effective way to move the tooth would be to locate the post on the mesiogingival tie-wings and apply the force in that direction. To do that, however, the appliance would have to be replaced. Replacement of an appliance during treatment is time consuming, expensive, and uncomfortable for the patient and, therefore, is generally avoided.

Ceramic appliances have presented additional problems in using posts or hooks. Unlike hooks or posts on metal appliances, ceramic hooks or posts cannot be made nearly as small as their metal counterparts. If a hook or post on a ceramic appliance were made in the same size and shape as known metal hooks or posts, it would likely fracture easily under the forces normally exerted on the appliance. Therefore, because of the relatively brittle nature of ceramics, ceramic appliances must be dimensioned and shaped appropriately to withstand the forces exerted upon them. Ceramic hooks or posts have therefore typically been larger and bulkier than metal hooks or posts.

In FIG. 1, a known ceramic appliance having an integral hook member is indicated generally by the reference numeral 1. The ceramic appliance 1 includes a pair of left tie-wings 2 and a pair of right tie-wings 3. The gingival side of the tie-wings 3 is formed into an integral hook member 4. The hook member 4 is formed by extending the tie-wing 3 in the gingival direction. The hook member 4 has formed on its free end an expanded portion 5.

Although the end of the hook member 4 is relatively thick in comparison to known metal hooks, the extended hook member is still often a weak point in the ceramic appliance and, therefore, prone to fracture. The expanded cross-sectional shape of the hook is also frequently impinged by the patient's facial musculature. Moreover, because the hook member 4 is located only on one side of the appliance, the same problems arise as with metal appliances having a single hook when the direction of the force exerted by the appliance should be reversed during treatment. To optimally transmit the appliance's force, a new appliance having the hook formed on the opposite tie-wings should be installed. Therefore, another drawback of such appliances is that an orthodontist is generally required to maintain a large inventory of different types of appliances. Because ceramic appliances are relatively expensive, most orthodontists would prefer to maintain fewer on hand.

Another known ceramic appliance having an integral hook or post is shown in FIG. 2, and is indicated generally by the reference numeral 6. The appliance 6 has formed on one side thereof a pair of split tie-wings or lugs 7, and has formed on the other side thereof an integral hook member 8. The hook member 8 extends substantially across the entire gingival side of the appliance 6, and has formed in the middle portion thereof a constricted section 9 for the attachment of ligature or other orthodontic appliances thereto.

One problem with the appliance 6 is that the single hook member 8 is relatively bulky and, therefore, it is likely to impinge on the soft tissue in a patient's mouth. Use of the appliance 6 is therefore likely to cause a patient additional discomfort. Because the appliance 6 has twin edgewise lugs or tie-wings to facilitate rotational control of the tooth during treatment, the tie-wings should be located on both sides of the appliance. The lugs or tie-wings 7, however, are formed only on one side of the appliance. Therefore, rotational control of the tooth will likely be inhibited.

In FIGS. 3 and 4, another known ceramic orthodontic appliance is indicated generally by the reference numeral 6. The appliance 6 of FIGS. 3 and 4 is similar to the appliance of FIG. 2 and, therefore, like reference numerals are used to indicate like elements. The appliance 6 is a twin-edgewise appliance and has formed on either side of the archwire slot a pair of split tie-wings or lugs 7. A hook member 8 projects outwardly from one of the tie-wings 7 in the gingival direction. The hook member has formed on the inside surface thereof an indentation 9 for the attachment of ligature or other orthodontic appliances thereto.

One problem with the appliance 6 is that because there is only one hook member 8, it is only possible to apply the auxiliary force in one direction. Another problem is that the hook member 8 extends outwardly beyond the end of the opposite tie-wing 7. Because it projects outwardly, and because of the brittle nature of ceramic material, the hook member 8 is prone to fracture. Moreover, because there is only a single indentation 9, an auxiliary appliance is likely to become dislodged from the hook member 8 when the teeth are brushed, or while chewing food.

It is an object of the present invention, therefore, to overcome the problems and drawbacks of known orthodontic appliances employing hooks or posts.

SUMMARY OF THE INVENTION

The present invention is directed to an orthodontic appliance for attachment to a tooth. The appliance comprises a bracket portion that defines an archwire slot therein. The appliance further comprises at least one first tie-wing projecting outwardly from the bracket portion on one side of the archwire slot. Two second tie-wings of the appliance project outwardly from the bracket portion on the other side of the archwire slot. The second tie-wings define an aperture therebetween and extending therethrough. The aperture is substantially circular and thus defined by a radius, and each second tie-wing includes a surface having a curvature substantially defined by the radius. Each curved surface is adapted to receive a force transmitting member connectable to another orthodontic appliance for transmitting forces thereto.

One orthodontic appliance of the present invention includes two first tie-wings. Each first tie-wing projects outwardly from the bracket portion. The first tie-wings are spaced apart from each other and extend along one side of the archwire slot. The bracket portion further defines a channel therein. The channel extends between the first tie-wings and between the second tie-wings in a direction substantially perpendicular to the axial direction of the archwire slot.

The present invention is directed to another orthodontic appliance for attachment to a tooth. The appliance comprises a bracket portion defining an archwire slot therein adapted to receive an archwire. The appliance further comprises two first tie-wings extending outwardly from the bracket portion on one side of the archwire slot. Two second tie-wings of the appliance extend outwardly from the bracket portion on the other side of the archwire slot. The two second tie-wings define a substantially circular aperture located therebetween and extending therethrough. The circular aperture is thus defined by two force transmitting surfaces. Each force transmitting surface is defined by a respective second tie-wing and has a curvature defined by the radius of the circular aperture. Each force transmitting surface is therefore adapted to receive an auxiliary force transmitting member to apply an auxiliary force thereto.

In one orthodontic appliance of the present invention, the free or gingival end of each second tie-wing is spaced apart from the other to permit a force transmitting member to pass therethrough and to be seated against a force transmitting surface. The distance between the free or gingival ends of the two second tie-wings is about equal to the radius of the circular aperture.

One advantage of the present invention is that the appliance can ordinarily perform the same functions of known appliances having hooks or posts, while not adding the additional bulk to the appliance normally associated therewith. Indeed, the appliance of the present invention has a profile similar to an ordinary twin edgewise, tie-wing appliance. Each force transmitting surface is located on an interior surface of the respective second tie-wing. As a result, there is not a relatively bulky portion for receiving a force transmitting member, as with known ceramic appliances having hooks or posts, that will likely impinge on the tissue in a patient's mouth. Therefore, most patients will usually not notice the difference between the appliance of the present invention and a similar known appliance not having a hook or post.

Another advantage of the present invention is that if the appliance is made of ceramic material, there is no need to add a larger or bulkier hook or post in order to withstand the ordinary forces exerted on the appliance, as with known ceramic appliances. Here, because the means for receiving a force transmitting member is located on an interior surface of each second tie-wing, there is no need for an extended hook or post. Accordingly, the second tie-wings, which do not need to be larger than most known ceramic tie-wings, will normally provide sufficient strength to withstand the ordinary forces exerted on the appliance.

Yet another advantage of the present invention is that the appliance may be employed to apply a force from a force transmitting member in more than one direction during the course of treatment. As described above, with known appliances employing a single hook, if it is necessary during treatment to reverse the direction of the force applied to the hook, the appliance would ordinarily have to be replaced with one having a hook located on the opposite side of the appliance. With the appliance of the present invention, on the other hand, each second or hooked tie-wing has a curved surface adapted for receiving a force transmitting member. Therefore, if the direction of the force needs to be reversed during treatment, the orthodontist can simply attach the force transmitting member to the other second or hooked tie-wing.

Other advantages of the present invention will become apparent in view of the following detailed description and drawings taken in connection therewith.

BRIEF DESCRIPTION OF THE DRAWINGS

FIG. 3 is a top plan view of another known orthodontic appliance having an integral hook member.

FIG. 4 is a side plan view of the appliance of FIG. 3.

FIG. 6 is a cross-sectional view of the appliance of FIG. 5 taken along the line A—A.

FIG. 10 is a top plan view of another orthodontic appliance embodying the present invention.

DETAILED DESCRIPTION

Figure 5:
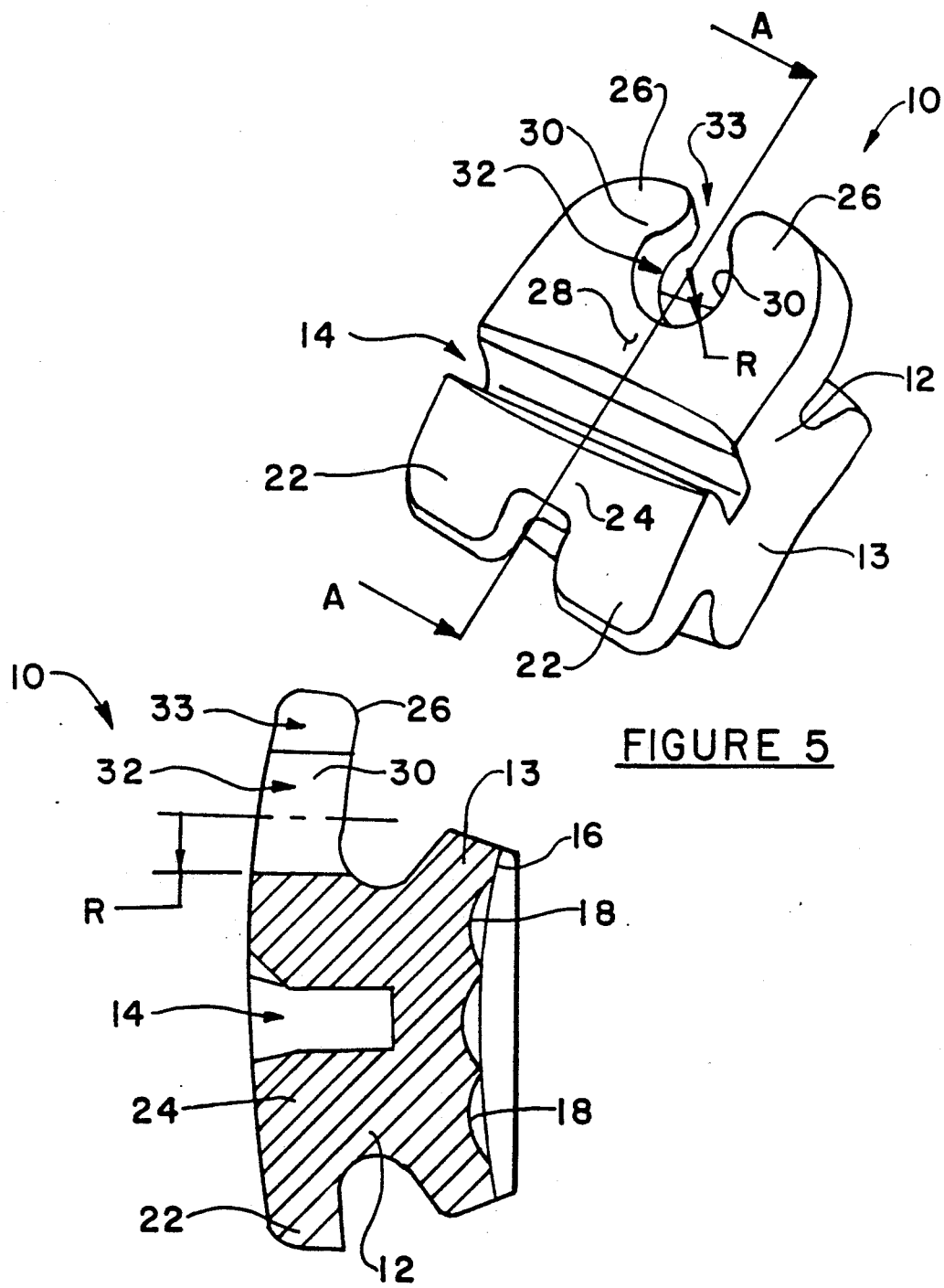
FIG. 5 is a top perspective view of an orthodontic appliance embodying the present invention.

In FIGS. 5 and 6, an orthodontic appliance embodying the present invention is indicated generally by the reference numeral 10. The orthodontic appliance 10 comprises a bracket portion 12 and a base portion 13. The bracket portion 12 defines an archwire slot 14 therein for receiving an archwire (not shown). The base portion 13 defines on the bottom thereof a tooth-abutting surface 16. The surface 16 is shaped generally to fit the morphology of a tooth, and has formed therein a plurality of indentations 18, for receiving adhesive material for mounting the appliance to a tooth.

Although the tooth-abutting surface 16 is shown with indentations, it may also take the shape of a number of known tooth-abutting surfaces. For example, the surface 16 may be smooth, or may have grooves formed therein. The appliance 10 is made of a ceramic material, such as a single crystal or polycrystalline aluminum oxide. The present invention is not limited to ceramic appliances, however, but may equally be employed in metal orthodontic appliances or appliances made of other materials, such as plastic.

The appliance 10 further includes a pair of split, or twin edgewise tie-wings 22, extending along one side of the bracket portion 12 and projecting outwardly therefrom. The tie-wings 22 are coupled to one another by a first web portion 24 extending along the adjacent edge of the archwire slot 14. A pair of hooked tie-wings 26 extend along the bracket portion 12 on the side opposite the tie-wings 22, and project outwardly therefrom. A second web portion 28 extends between the hooked tie-wings 26 along the adjacent edge of the archwire slot 14.

Each hooked tie-wing 26 defines on an interior side thereof a hook-shaped surface 30. The opposing hooked surfaces 30 define therebetween a round aperture 32 having a radius R. The two surfaces 30 meet at about the middle of the web portion 28 and thus form a single curved surface defined substantially by the radius R. The center of the radius R is located about midway between the mesial and distal edges of the bracket portion 12.

As shown in FIG. 6, the inside perimeter of the round aperture 32 substantially coincides with the plane of the gingival side of the bracket portion 12. Therefore, either hook-shaped tie-wing 26 is not likely to fracture if a strong impact force is applied thereto. A narrow opening 33 is defined between the tips of the two hooked tie-wings 26. The opening 33 is wide enough to permit an elastic, ligature wire, or auxiliary force transmitting member to be passed therethrough and seated against either hook-shaped surface 30. However, the opening 30 is narrow enough to prevent such members from becoming dislodged when, for example, the teeth are brushed or the patient is chewing food. In one embodiment of the appliance 10, the width of the opening 33 is about equal to the radius R of the aperture 32.

The free end of each hooked tie-wing 26, which is generally the gingival end, is formed with a rounded contour to facilitate the attachment of ligature, elastics, coil springs, or other force transmitting members thereto. The rounded ends are also provided to avoid any sharp corners that might cause discomfort by impinging on the tissue in a patient's mouth. Another advantage of the rounded free ends is that they avoid the formation of points of concentrated stress that tend to easily fracture.

The appliance 10 is mounted to a tooth by applying adhesive material to the tooth-abutting surface 16. Ordinarily, the appliance 10 is oriented on the tooth so that the hooked tie-wings 26 are placed on the gingival side of the tooth. The hooked tie-wings 26 can then serve substantially the same purposes as hooks or posts on known orthodontic appliances. For example, ligature or elastics can be wrapped or fitted over either of the hooked tie-wings 26, and seated on the respective hook-shaped surface 30. The hooked end of a coil spring, or other auxiliary appliance, can also be coupled to one of the hooked tie-wings 26, and seated against the respective hook-shaped surface 30, to transmit the auxiliary force thereto.

Figure 7:
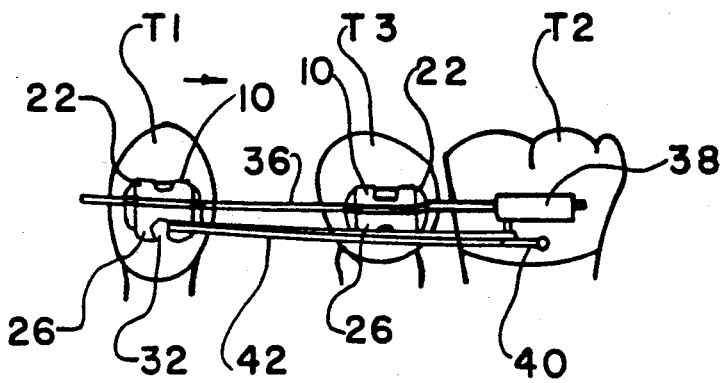
FIG. 7 is a side plan view of two of the orthodontic appliances of FIG. 5 mounted to a patient's teeth, one being coupled to an auxiliary appliance.
Figure 8:
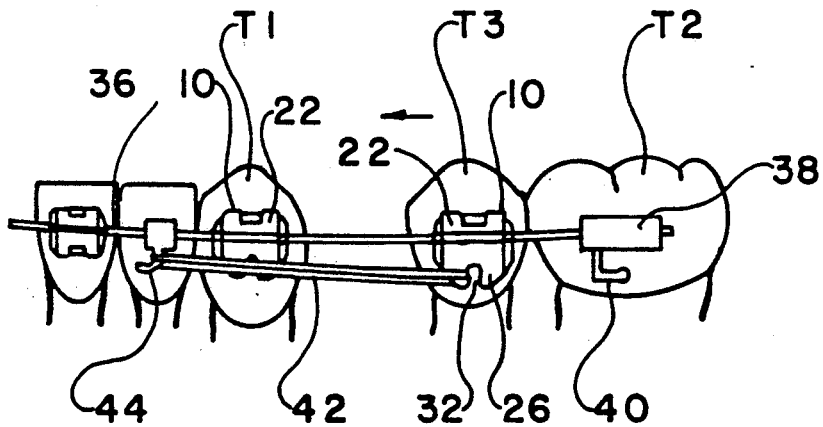
FIG. 8 is another side plan view of two orthodontic appliances of FIG. 5 mounted to a patient's teeth, one being coupled to an auxiliary appliance.

In FIGS. 7 and 8, two orthodontic appliances 10 are shown mounted to teeth T1 and T3 with an archwire 36 ligated thereto. A molar tube 38 having a gingival hook 40 is mounted to the molar T2 and ligated to the archwire 36. An elastic ring 42 is coupled between the distal hooked tie-wing 26 on the cuspid T1 and the hook 40 on the molar tube 38. The elastic ring 42 therefore applies a distally directed force to the cuspid T1, as indicated by the arrow in FIG. 7. In FIG. 8, a hook 44 is coupled to the archwire 36. An elastic ring 42 is coupled between the mesial hooked tie-wing 26 on the bicuspid T3 and the hook 44. The elastic ring 42 therefore applies a mesially directed force to the bicuspid T3, as indicated by the arrow in FIG. 8.

Therefore, as illustrated in FIGS. 7 and 8, it is possible to use an orthodontic appliance 10 to selectively shift a tooth in different directions. Although not illustrated, it is also possible to connect an elastic ring 42, or other auxiliary appliance, between the hooked tie-wings 26 of two adjacent appliances 10. Because the elastic ring 42 is seated within the round aperture 32, and against one of the hook-shaped surfaces 30, the problem of the elastic ring becoming dislodged from the bracket is ordinarily avoided. The hook-shaped curvature of the surface 30 and the relatively narrow opening 33 function to prevent the elastic ring from becoming accidentally dislodged during treatment.

Figure 1:
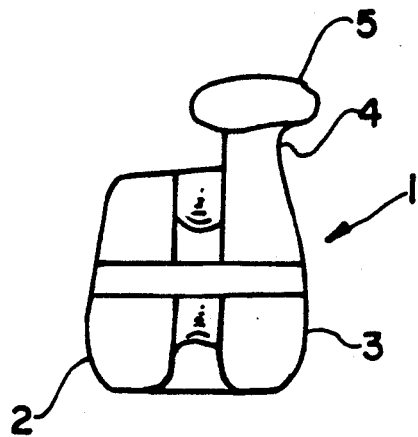
FIG. 1 is a top plan view of a known ceramic orthodontic appliance having an integral hook member.

Because the same appliance 10 may be used for applying forces in more than one direction, the orthodontist does not have to purchase different types of ceramic appliances depending upon the direction in which the force of the appliance is to be applied. Therefore, an orthodontist using the appliance 10 will usually be able to retain a smaller inventory of ceramic appliances on hand. Another advantage of the present invention is that the hooked tie-wings 26 have proven to be sturdier than the hooks that are formed on known ceramic appliances, such as by extending one tie-wing outwardly into a hooked-shape, as shown in FIG. 1. The appliance 10 is therefore less likely to fracture.

Figure 2:
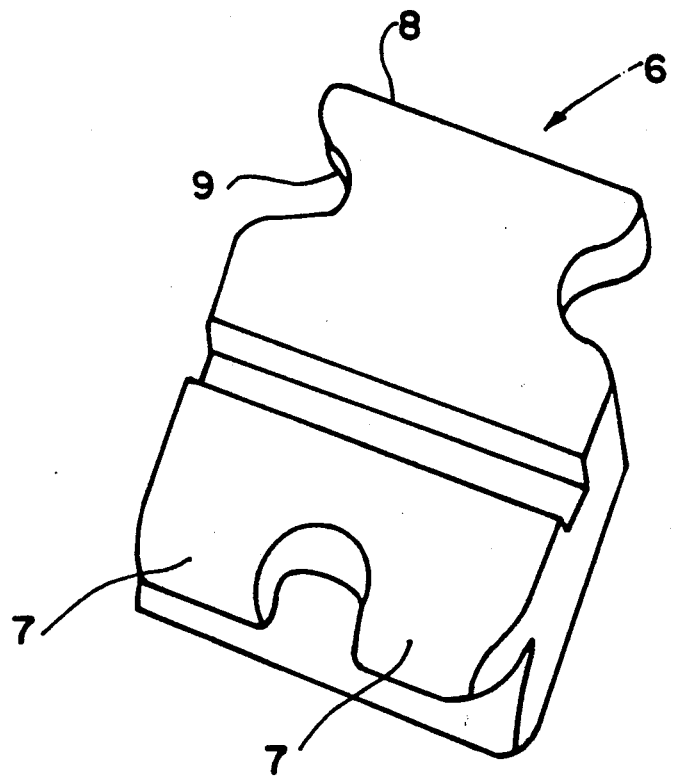
FIG. 2 is a top perspective view of another known ceramic orthodontic appliance having an integral hook member.

Yet another advantage of the present invention is that the hooked tie-wings 26 are shaped to be functionally similar not only to hooks or posts used in known appliances, but also to tie-wings, such as the tie-wings 22. As shown in FIG. 5, the hooked tie-wings 26 have a similar profile to the ordinary twin edgewise tie-wings 22. Therefore, like the tie-wings 22, the hooked tie-wings 26 can be used to ligate an archwire seated in the archwire slot 14 to rotationally control the tooth. On the other hand, known ceramic appliances that do not have a split tie-wing shape, such as the appliance of FIG. 2, will likely inhibit rotational control of the tooth.

It should also be noted that because the hooked tie-wings 26 have a profile similar to that of the split tie-wings 22, the hooked tie-wings ordinarily will not cause further discomfort to the patient. On the other hand, known appliances having tie-wings with hooks or posts projecting outwardly therefrom, are more likely to impinge the tissue in a patient's mouth.

Figure 9:
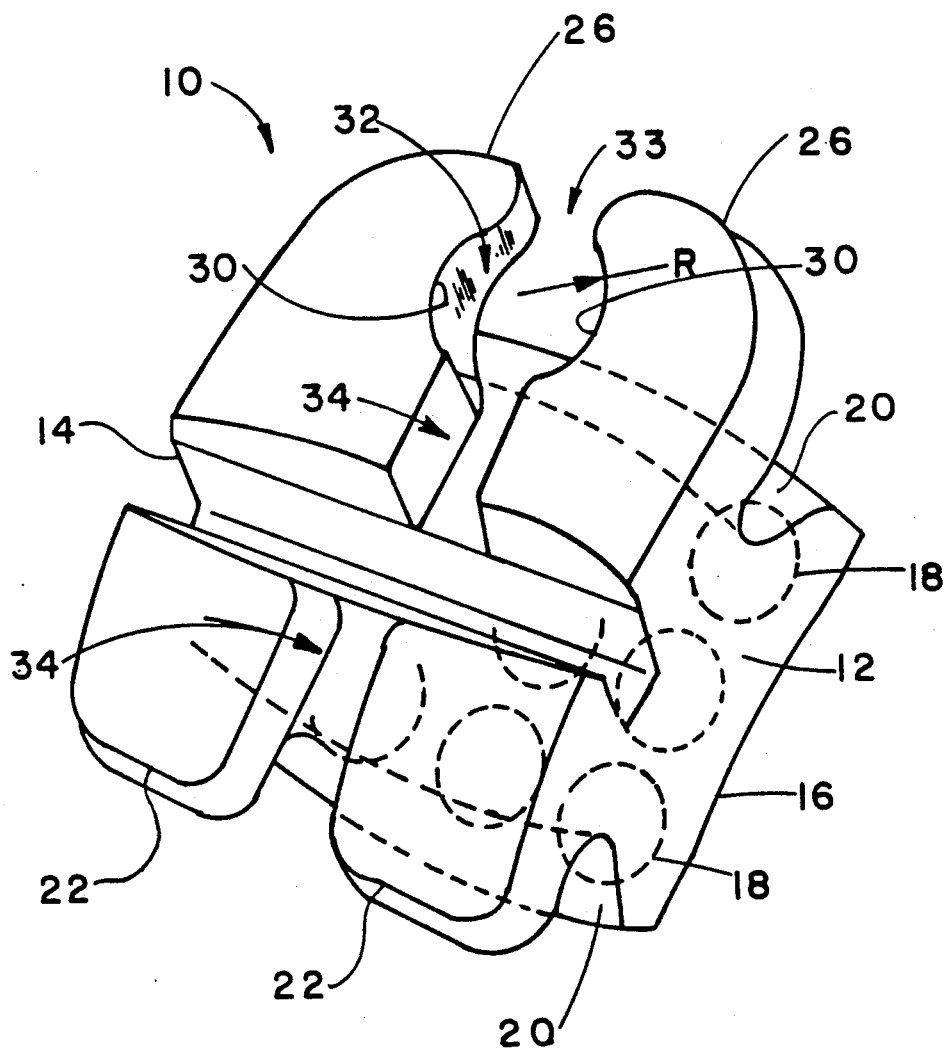
FIG. 9 is a top perspective view of another orthodontic appliance embodying the present invention.

In FIG. 9, another orthodontic appliance embodying the present invention is indicated generally by the reference numeral 10. The appliance 10 of FIG. 9 is similar to the appliance 10 of FIGS. 5 and 6 and, therefore, like reference numerals are used to indicate like elements. The appliance 10 of FIG. 9 is different in that neither the split tie-wings 22, nor the hooked tie-wings 26, are coupled by web portions. Instead, a channel 34 is formed between the split tie-wings 22 and the hooked tie-wings 26, which extends across the appliance in a direction substantially perpendicular to the axial direction of the archwire slot 14.

The hooked surfaces 30 define therebetween a round aperture 32 having a radius R. The two hooked surfaces 30 are therefore defined by the radius R. The center of the radius R is located about midway between the mesial and distal edges of the bracket portion 12. However, the channel 34 extends through the aperture 32. The width of the opening 33 between the tips of the tie-wings 26 is preferably about equal to the radius R. The channel 34 facilitates ligating an archwire to either the split tie-wings 22, or the hooked tie-wings 26. However, it should be noted that the round aperture 32 in the appliance of FIGS. 5 and 6 can also be used to achieve the results of a split tie-wing appliance. The hooked tie-wings 26 in FIG. 9 can otherwise be used in the same manner as the hooked tie-wings described above in relation to FIGS. 5 and 6.

In FIG. 10, another orthodontic appliance embodying the present invention is indicated generally by the reference numeral 10. The appliance 10 of FIG. 10 is similar to the appliance 10 of FIGS. 5 and 6. Therefore, like reference numerals are used to indicate like elements. The appliance 10 of FIG. 10 is different in that the mesial and distal edges of the appliance are slanted at an angle relative to the longitudinal (or mesial-distal) axis of the archwire slot 14. The appliance 10 is called a cuspid bracket, because its shape is particularly suitable for the treatment of cuspids. Accordingly, as will be recognized by those skilled in the art, the orthodontic appliance of the present invention can take a variety of shapes and relative dimensions.

What is claimed is:

1. An orthodontic appliance for attachment to a tooth, comprising:
   a bracket portion defining an archwire slot therein adapted to receive an archwire;
   at least one first tie-wing projecting outwardly from the bracket portion on one side of the archwire slot; and
   two second tie-wings projecting outwardly from the bracket portion on the other side of the archwire slot, the second tie-wings defining an aperture therebetween and extending therethrough, the aperture being substantially circular and thus defined by a radius, each second tie-wing including a surface having a curvature substantially defined by the radius, each curved surface being adapted to receive means for transmitting an auxiliary force to the appliance.

2. An orthodontic appliance as defined in claim 1, wherein
   the appliance includes a ceramic material.

3. An orthodontic appliance as defined in claim 1, wherein
   the appliance is made of metal.

4. An orthodontic appliance as defined in claim 1, including two first tie-wings, each first tie-wing projecting outwardly from the bracket portion, the first tie-wings being spaced apart from each other and extending along one side of the archwire slot.

5. An orthodontic appliance as defined in claim 4, wherein
   the bracket portion further defines a channel therein, and the channel extends between the first tie-wings and between the second tie-wings in a direction substantially perpendicular to the axial direction of the archwire slot.

6. An orthodontic appliance as defined in claim 1, wherein
   the appliance includes plastic.

7. An orthodontic appliance for attachment to a tooth, comprising:
   a bracket portion defining an archwire slot adapted to receive an archwire;
   at least one first tie-wing projecting outwardly from the bracket portion on one side of the archwire slot; and
   two second tie-wings projecting outwardly from the bracket portion on the other side of the archwire slot, each second tie-wing defining a hook-shaped surface, the two hook-shaped surfaces each facing the other and defining a first aperture extending therebetween, each hook-shaped surface being adapted to receive an auxiliary force transmitting member connectable to another orthodontic appliance.

8. An orthodontic appliance as defined in claim 7, wherein the first aperture is substantially circular and is thus defined by a radius.

9. An orthodontic appliance as defined in claim 8, wherein
the free ends of the two second tie-wings define a second aperture therebetween, the second aperture being adapted to pass a force transmitting member therethrough to be seated against either hook-shaped surface.

10. An orthodontic appliance as defined in claim 9, wherein
the width of the second aperture between the free ends of the two second tie-wings is about equal to the radius of the first aperture.

11. An orthodontic appliance as defined in claim 10, wherein
the two hook-shaped surfaces meet at a web portion extending between the two second tie-wings, and the surface of the web portion defining the first aperture substantially coincides with the plane of a gingival surface of the bracket portion.

12. An orthodontic appliance as defined in claim 8, wherein
the center of the radius of the first aperture is located about midway between the mesial and distal sides of the bracket portion.

13. An orthodontic appliance for attachment to a tooth, comprising:
a bracket portion having an archwire slot formed therein; and
two hooked tie-wings located on one side of the archwire slot and projecting outwardly from the bracket portion, each hooked tie-wing defining a force transmitting surface facing the other hooked tie-wing, the two force transmitting surfaces defining an aperture therebetween and extending through the two hooked tie-wings, each force transmitting surface having a curvature substantially defined by a radius and thus being adapted to receive an auxiliary force transmitting member connectable to another appliance.

14. An orthodontic appliance as defined in claim 13, wherein
the aperture is substantially circular and thus defined by a radius, which in turn substantially defines the curvature of each force transmitting surface.

15. An orthodontic appliance as defined in claim 14, further comprising:
a web portion extending between the two hooked tie-wings and located adjacent to the archwire slot, the side of the web portion opposite the archwire slot having a curvature defined by the radius of the aperture.

16. An orthodontic appliance as defined in claim 15, wherein the center of the radius of the aperture is located about midway between the mesial and distal sides of the bracket portion.

17. An orthodontic appliance as defined in claim 13, wherein
an exterior surface on the free or gingival end of each hooked tie-wing is rounded, and each hooked tie-wing thus defines a substantially hooked-shape.

18. An orthodontic appliance as defined in claim 13, wherein
the free or gingival ends of the two hooked tie-wings are spaced apart from each other a distance less than the distance between the two force transmitting surfaces.

19. An orthodontic appliance for attachment to a tooth, comprising:
a bracket portion having an archwire slot formed therein adapted to receive an archwire; and
two tie-wings located on one side of the archwire slot and projecting outwardly from the bracket portion, the two tie-wings defining an aperture located therebetween and extending therethrough, each tie-wing including a force transmitting surface facing the other defining means for transmitting an auxiliary force thereto.

20. An orthodontic appliance as defined in claim 19, wherein
each force transmitting surface has a curvature defined substantially by a radius.

21. An orthodontic appliance as defined in claim 20, wherein
the aperture is substantially circular and thus defined by a radius, and the radius in turn substantially defines the curvature of each force transmitting surface.

22. An orthodontic appliance as defined in claim 21, further comprising:
a web portion located adjacent to the archwire slot and extending between the two tie-wings, wherein a surface of the web portion defines the common boundary of the two force transmitting surfaces.

23. An orthodontic appliance as defined in claim 22, wherein
the surface defining the common boundary of the two force transmitting surfaces is substantially coincident with the plane of a gingival surface of the bracket portion.

24. An orthodontic appliance as defined in claim 21, wherein
the center of the radius of the circular aperture is located about midway between the mesial and distal sides of the bracket portion.

25. An orthodontic appliance as defined in claim 20, wherein
an exterior surface located on the free or gingival end of each tie-wing is rounded, thus forming a substantially hooked-shape.

26. An orthodontic appliance as defined in claim 20, wherein
the free or gingival ends of the two tie-wings are spaced apart from each other a distance less than the distance between the two force transmitting surfaces.

27. An orthodontic appliance for attachment to a tooth, comprising:
a bracket portion defining an archwire slot therein adapted to receive an archwire;
two first tie-wings extending outwardly from the bracket portion on one side of the archwire slot;
two second tie-wings extending outwardly from the bracket portion on the other side of the archwire slot, the two second tie-wings defining a substantially circular aperture located therebetween and extending therethrough, the circular aperture being defined by two force transmitting surfaces, each force transmitting surface being defined by a respective second tie-wing and having a curvature defined by the radius of the circular aperture, each force transmitting surface thus being adapted to receive an auxiliary force transmitting member to apply an auxiliary force thereto.

28. An orthodontic appliance as defined in claim 27, wherein
the free or gingival end of each second tie-wing is spaced apart from the other to permit a force transmitting member to pass therethrough and be seated against a force transmitting surface.

29. An orthodontic appliance as defined in claim 28, wherein
the distance between the free or gingival ends of the two second tie-wings is about equal to the radius of the circular aperture.

30. An orthodontic appliance for attachment to a tooth, comprising:
a bracket portion having an archwire slot formed therein and adapted to receive an archwire;
two first tie-wings projecting from the bracket portion on one side of the archwire slot;
two hooked tie-wings spaced apart from each other and projecting from the opposite side of the archwire slot, each hooked tie-wing defining a hook-shaped surface, the two hook-shaped surfaces each facing the other and defining an aperture therebetween extending through the two hooked tie-wings, each hook-shaped surface having a curvature defined substantially by one radius, the two hook-shaped surfaces thus each being adapted to receive an auxiliary force transmitting member to apply an auxiliary force thereto.

31. An orthodontic appliance as defined in claim 30, wherein
the aperture is substantially circular and the distance between the free ends of the two hooked tie-wings is about equal to the radius of the circular aperture.

32. An orthodontic appliance as defined in claim 31, wherein
the exterior surface of the free end of each hooked tie-wing has a curvature giving each hooked tie-wing a substantially hooked-shape.

33. An orthodontic appliance as defined in claim 31, wherein
a mesial surface and a distal surface of the bracket portion are oriented in a parallel relationship relative to each other and at an acute angle relative to the mesial-distal axis of the archwire slot.

* * * * *

UNITED STATES PATENT AND TRADEMARK OFFICE
CERTIFICATE OF CORRECTION

PATENT NO. : 5,030,089

DATED : July 9, 1991

INVENTOR(S) : Kozo KAWAGUCHI

It is certified that error appears in the above-identified patent and that said Letters Patent is hereby corrected as shown below:

Column 9, line 55, beginning with "the center of the radius" through the end of the paragraph should be a new paragraph. and indented.

Signed and Sealed this

Sixteenth Day of February, 1993

Attest:

STEPHEN G. KUNIN

Attesting Officer

Acting Commissioner of Patents and Trademarks